United States Patent
Fugerer et al.

(10) Patent No.: US 12,290,274 B2
(45) Date of Patent: May 6, 2025

(54) DYNAMICALLY CONTROLLING A DISTAL WINDOW OPENING IN A ROTARY SURGICAL SHAVER

(71) Applicant: ARTHREX, INC., Naples, FL (US)

(72) Inventors: Robert Fugerer, Lutz, FL (US); Brett Poole, St. Pete Beach, FL (US); Joshua Buckman, St. Pete Beach, FL (US); Ankur Vayeda, St. Pete Beach, FL (US); Jefferey Slater, Naples, FL (US)

(73) Assignee: Arthrex, Inc., Naples, FL (US)

( * ) Notice: Subject to any disclaimer, the term of this patent is extended or adjusted under 35 U.S.C. 154(b) by 203 days.

(21) Appl. No.: 17/329,999

(22) Filed: May 25, 2021

(65) Prior Publication Data

US 2022/0378457 A1 Dec. 1, 2022

(51) Int. Cl.
*A61B 17/32* (2006.01)
*G16H 40/63* (2018.01)
(Continued)

(52) U.S. Cl.
CPC ....... *A61B 17/32002* (2013.01); *G16H 40/63* (2018.01); *A61B 2017/00017* (2013.01);
(Continued)

(58) Field of Classification Search
CPC .. A61B 17/32002; A61B 2017/320032; A61B 2090/0811; A61B 2017/00022;
(Continued)

(56) References Cited

U.S. PATENT DOCUMENTS

| 4,345,192 A | 8/1982 | Kohzai et al. |
| 4,705,038 A | 11/1987 | Sjostrom et al. |

(Continued)

FOREIGN PATENT DOCUMENTS

| CN | 109303592 | 2/2019 |
| WO | 2017095679 | 6/2017 |

OTHER PUBLICATIONS

Occam MD, "Stryker CORE System Console and Handpiece Benchmarking Report," Dated Nov. 30, 2015, document of 122 pages.
(Continued)

*Primary Examiner* — Shaun L David
*Assistant Examiner* — Mitchell Brian Hoag
(74) *Attorney, Agent, or Firm* — Greenberg Traurig, LLP; Michael K. Dixon (57) ABSTRACT

A medical device system configured to dynamically control a shaver window opening via controlling positioning of an opening in an inner drive shaft relative to an opening in an outer housing based on continuously tracking the motor is disclosed. The medical device system may include a shaver at a distal end and an aspiration system configured to aspirate material through the inner drive shaft. A processor of the medical device system may control rotational motion of the inner drive shaft based on continuously sensing the position of the opening in the inner drive shaft to reduce clogs and increase cutting effectiveness of the system. By continuously monitoring the medical device system, the processor can correct out of phase conditions in oscillation mode to prevent poor cutting conditions. The processor can also dynamically determine a reversal position on the opening in the inner drive shaft to create a desired cutting action.

24 Claims, 4 Drawing Sheets

(51) Int. Cl.
    *A61B 17/00* (2006.01)
    *A61B 17/3207* (2006.01)
    *A61B 90/00* (2016.01)

(52) U.S. Cl.
    CPC ............... *A61B 2017/00022* (2013.01); *A61B 2017/320024* (2013.01); *A61B 2017/320028* (2013.01); *A61B 2017/320032* (2013.01); *A61B 2017/32004* (2013.01); *A61B 2017/320064* (2013.01); *A61B 17/320758* (2013.01); *A61B 2017/320766* (2013.01); *A61B 2017/320775* (2013.01); *A61B 17/320783* (2013.01); *A61B 2090/0811* (2016.02)

(58) Field of Classification Search
    CPC ......... A61B 2017/00017; A61B 2017/320028; A61B 17/320758; A61B 2017/320766; A61B 2017/320775; A61B 17/320783; A61B 2017/320024
    See application file for complete search history.

(56) References Cited

U.S. PATENT DOCUMENTS

| | | | |
|---|---|---|---|
| 4,867,155 A | 9/1989 | Isaacson | |
| 4,995,877 A | 2/1991 | Ams et al. | |
| 5,030,900 A | 7/1991 | Kono | |
| 5,602,449 A | 2/1997 | Kruse | |
| 5,632,759 A | 5/1997 | Rexroth | |
| 5,669,921 A | 9/1997 | Berman et al. | |
| 6,451,017 B1* | 9/2002 | Moutafis | A61B 17/32037 604/35 |
| 6,743,245 B2 | 6/2004 | Lobdell | |
| 7,438,705 B2 | 10/2008 | Karpowicz et al. | |
| 7,510,542 B2 | 3/2009 | Blight | |
| 7,717,931 B2 | 5/2010 | Himes | |
| 7,758,538 B2 | 7/2010 | Boukhny et al. | |
| 7,998,157 B2 | 8/2011 | Culp et al. | |
| 8,226,677 B2 | 7/2012 | Kauker et al. | |
| 8,262,603 B2 | 9/2012 | Shener et al. | |
| 8,409,235 B2 | 4/2013 | Rubin | |
| 8,568,418 B2* | 10/2013 | Matusaitis | A61B 17/32002 606/180 |
| 9,028,398 B2 | 5/2015 | Kumar et al. | |
| 9,050,123 B2 | 6/2015 | Krause et al. | |
| 9,233,193 B2 | 1/2016 | Truckai et al. | |
| 9,295,477 B2 | 3/2016 | Schneider et al. | |
| 9,308,315 B2 | 4/2016 | Stubkjaer et al. | |
| 9,370,611 B2 | 6/2016 | Ross et al. | |
| 9,451,977 B2 | 9/2016 | Schmitz et al. | |
| 9,456,872 B2 | 10/2016 | Hendrick et al. | |
| 9,511,184 B2 | 12/2016 | Woolford et al. | |
| 9,737,362 B2 | 8/2017 | Germain et al. | |
| 9,814,484 B2 | 11/2017 | Schmitz et al. | |
| 9,855,383 B2 | 1/2018 | Shener et al. | |
| 9,883,885 B2 | 2/2018 | Hendrick et al. | |
| 9,907,563 B2 | 3/2018 | Germain et al. | |
| 9,999,466 B2 | 6/2018 | Germain et al. | |
| 10,064,644 B2 | 9/2018 | Schmitz et al. | |
| 10,137,034 B2 | 11/2018 | Heeren | |
| 10,213,246 B2 | 2/2019 | Toth et al. | |
| 10,335,180 B2 | 7/2019 | Johnson et al. | |
| 10,383,691 B2 | 8/2019 | Hendrick et al. | |
| 10,405,924 B2 | 9/2019 | Bowe | |
| 10,485,613 B2 | 11/2019 | Hendrick et al. | |
| 10,595,882 B2 | 3/2020 | Parfett et al. | |
| 11,547,815 B2* | 1/2023 | Minahan | A61B 1/018 |
| 2005/0085838 A1* | 4/2005 | Thompson | A61B 10/0275 606/170 |
| 2009/0018566 A1* | 1/2009 | Escudero | A61B 17/3207 606/159 |
| 2010/0049225 A1* | 2/2010 | To | A61B 17/320758 606/159 |
| 2010/0100112 A1* | 4/2010 | Kauker | A61B 17/32002 606/180 |
| 2011/0112563 A1* | 5/2011 | To | A61B 17/320783 604/528 |
| 2012/0022526 A1* | 1/2012 | Aldridge | A61B 18/1445 606/45 |
| 2013/0060278 A1* | 3/2013 | Bozung | A61B 17/3403 606/205 |
| 2013/0085498 A1 | 4/2013 | Matusaitis et al. | |
| 2013/0110145 A1* | 5/2013 | Weitzman | A61B 17/1642 606/170 |
| 2014/0114336 A1* | 4/2014 | Schmitz | A61B 17/32002 606/170 |
| 2014/0276949 A1* | 9/2014 | Staunton | F16D 1/116 606/130 |
| 2015/0125807 A1* | 5/2015 | Shipley | A61C 3/02 433/215 |
| 2015/0201956 A1* | 7/2015 | Higgins | A61B 17/320725 606/159 |
| 2017/0065396 A1* | 3/2017 | Look | A61B 17/32037 |
| 2017/0333052 A1* | 11/2017 | Ding | A61B 17/00234 |
| 2018/0214171 A1* | 8/2018 | Ryan, Jr. | A61B 17/3421 |
| 2019/0059983 A1* | 2/2019 | Germain | A61B 17/1606 |
| 2019/0105072 A1* | 4/2019 | Govari | A61B 34/20 |
| 2019/0143010 A1 | 5/2019 | Gaspredes et al. | |
| 2019/0175211 A1* | 6/2019 | Carlson | A61B 17/320758 |
| 2019/0201058 A1* | 7/2019 | Arnin | A61B 17/7071 |
| 2019/0201082 A1* | 7/2019 | Shelton, IV | G05B 19/0428 |
| 2019/0201083 A1 | 7/2019 | Shelton et al. | |
| 2019/0201085 A1 | 7/2019 | Shelton et al. | |
| 2019/0223898 A1 | 7/2019 | Curtin et al. | |
| 2019/0262022 A1* | 8/2019 | Spangler | A61B 34/76 |
| 2019/0262034 A1* | 8/2019 | Spangler | A61B 17/320758 |
| 2019/0321063 A1* | 10/2019 | Germain | A61B 18/148 |
| 2019/0355936 A1* | 11/2019 | To | A61B 17/320758 |
| 2019/0388117 A1* | 12/2019 | Akbarian | A61M 1/742 |
| 2020/0054356 A1* | 2/2020 | Miller | A61B 17/320758 |
| 2020/0146703 A1* | 5/2020 | Truckai | A61B 1/045 |
| 2020/0187768 A1* | 6/2020 | Shelton | A61B 18/24 |
| 2020/0330085 A1* | 10/2020 | Truckai | A61B 17/320068 |
| 2021/0353321 A1* | 11/2021 | Jezierski | A61B 17/32002 |
| 2021/0401448 A1* | 12/2021 | Masubuchi | A61B 90/03 |
| 2022/0249112 A1* | 8/2022 | Magno | A61B 90/08 |
| 2022/0387071 A1* | 12/2022 | To | A61B 17/320758 |

OTHER PUBLICATIONS

Chen et al., "A review on surgical instruments of knee arthroscopic debridement and total hip arthroplasty," 3rd CIRP Conference on BioManufacturing, 2017, pp. 291-298.
Stryker, "Powered Instrument Driver, REF 5400-50," 2005, document of 37 pages.
Smith & Nephew, "Dyonics Power Shaver System," 2005, document of 52 pages.
Smith & Nephew, "Dyonics Power II Shaver System; Dyonics PowerMax Elite Handpiece," 2012, document of 7 pages.
United States Patent and Trademark Office; PCT International Search Report, Issued in Connection to PCT/US2022/30895; Oct. 3, 2022; 3 pages; US.
United States Patent and Trademark Office; PCT Written Opinion of the International Searching Authority, Issued in Connection to PCT/US2022/30895; Oct. 3, 2022; 10 pages; US.
"Design and characterization of a debriding tool in robot-assisted treatment of osteolysis"; Farshid Alambeigi et al.; May 2016, https://www.researchgate.net/profile/Farshid_Alambeigi/publication/303886247_Design_and_characterization_of_a_debriding_tool_in_robot-assisted_treatment_of_osteolysis/links/59dedd130f7e9bcfab246350/Design-and-characterization-of-a-debriding-tool-in-robot-assisted-treatment-of-osteolysis.pdf.
"Tissue model and preliminary analysis of microdebriders used in functional endoscopic sinus surgery"; Sandeep P. Dave et al.; Jun. 1, 2005, http://citeseerx.ist.psu.edu/viewdoc/download?doi=10.1.1.930.8847&rep=rep1&type=pdf.

* cited by examiner

DYNAMICALLY CONTROLLING A DISTAL WINDOW OPENING IN A ROTARY SURGICAL SHAVER

BACKGROUND

The disclosure relates generally to handheld, rotary medical devices, and more particularly, to handheld, rotary medical devices with shavers.

Handheld rotary medical devices include working ends, which are often shavers or burrs, that are configured for the removal of hard or soft tissue from the body. Many of these devices are configured to remove soft tissue. Current methods for controlling the window aperture of a shaver blade, also referred to as window-lock, focus on controlling fluid flow-rate in an aspiration system using a static aperture opening when the system is at rest. A fully closed aperture prevents fluid and debris from flowing, while a fully open aperture provides maximum flow. Partial aperture openings have various degrees of flow-rate restriction. In addition to controlling flow-rate, static window-lock is also used to reduce the chance of catching soft-tissue in the window during the insertion and removal of the shaver blade from the joint space.

Another issue that arises with shavers is that while operating a shaver in various oscillatory modes, the window aperture may open and close in an inconsistent manner, or in other cases, not at all. Such inconsistent function contributes to system clogging, cutting inefficiency, and inconsistent operation with respect to the intended use.

SUMMARY

A medical device system configured to dynamically control a shaver window opening via controlling alignment of an opening in an inner drive shaft relative to an opening in an outer housing based on continuously tracking of the motor is disclosed. The medical device system may include a shaver at a distal end and an aspiration system configured to aspirate material through the inner drive shaft. A processor of the medical device system may control rotational motion of the inner drive shaft based on continuously sensing the position of the opening in the inner drive shaft to reduce clogs and increase cutting effectiveness of the system. By continuously monitoring the medical device system, the processor can correct out of phase conditions in oscillation mode to prevent poor cutting conditions. The processor can also dynamically determine a reversal position of the opening in the inner drive shaft to create a desired cutting action. In at least one embodiment, the processor can also dynamically determine a reversal position of the opening in the inner drive shaft to create a maximum amount of momentum and torque.

In at least one embodiment, the medical device system may be formed from a handheld rotary medical device that may include a motor, an inner drive shaft coupled to the motor, and an elongated outer housing receiving the inner drive shaft such that the inner drive shaft is positioned within the outer housing. The handheld rotary medical device may include a shaver at a distal end of the inner drive shaft. The shaver may include one or more openings in an outer wall forming the inner drive shaft, and the outer housing may include an opening at a distal end that may be aligned longitudinally with the opening in the shaver at the distal end of the inner drive shaft. The medical device system may also include an aspiration system with a channel in the inner drive shaft. The medical device system may also include a processor configured to control driving of the motor and the inner drive shaft. The processor may be configured to dynamically control positioning of the opening in the inner drive shaft relative to the opening in the outer housing based on continuously tracking of the motor.

In at least one embodiment, the processor may be configured to operate the inner drive shaft in an oscillating mode whereby pulsed flow of aspirated material flows through the inner drive shaft to flush the inner drive shaft and prevent clogging. In addition, the processor may be configured to control the force of the pulsing action from a mild pulsing action to a more intense pulsing action by controlling one or more of the numerous variables of the oscillation mode, including but not limited to, speed, amount of window opening, a location of the reversal position and the like. The processor may be configured to operate the inner drive shaft in an oscillating mode whereby a reversal position for the inner drive shaft is sequenced to generate a pumping action from one of various pulsed flow intensities and rates to prevent clogging via reversal positions that may be varied during an oscillation mode. The rotational position of the reversal positions may be varied to create a desired degree of window alignment or misalignment at the reversal position.

In at least one embodiment, the processor may operate the inner drive shaft in an oscillating mode that reverses rotational direction of at least one window aperture opening. The processor may operate the inner drive shaft in an oscillating mode that reverses rotational direction of at least one window aperture opening using a vector which embodies time, rotation and position to define the reversal of direction in a manner that more consistently targets specific user performance parameters. In the oscillating mode, the inner drive shaft may stop at one of multiple of reversal positions before rotating in a reverse direction. In at least one embodiment, the processor may identify a reversal position for the inner drive shaft that generates maximum momentum for cutting material via the opening in the inner drive shaft.

In at least one embodiment, the processor may be configured such that continuous tracking of the motor by the processor enables the processor to control the inner drive shaft via an open loop system that controls the inner drive shaft based on desired cutting torque as a function of inner drive shaft opening position. Continuous tracking of the motor by the processor may enable the processor to control the inner drive shaft via an open loop system that controls the inner drive shaft based on desired flush cycles as a function of inner drive shaft opening position. Continuous tracking of the motor by the processor enables the processor to control the inner drive shaft via an open loop system that controls the inner drive shaft based on desired cutting debris flow rate as a function of inner drive shaft opening position.

In another embodiment, the processor may be configured such that continuous tracking of the motor by the processor enables the processor to control the inner drive shaft via a closed loop system that controls the inner drive shaft based on sensor input from the aspiration system. Continuous tracking of the motor by the processor may enable the processor to control the inner drive shaft via a closed loop system that controls the inner drive shaft based on sensor input of fluid flow rate in the aspiration system. Continuous tracking of the motor by the processor enables the processor to control the inner drive shaft via a closed loop system that controls the inner drive shaft based on sensor input of a fluid metric, such as, but not limited to, a measure of the consistency, viscosity or the like of the material in the aspiration system.

The processor may be configured to track revolutions of the opening in the inner drive shaft in each direction to correct out of phasing conditions thereby enabling more consistent control of an oscillation mode, which in turn stabilizes flow rate and cutting efficiency. The processor may control the motor for oscillation factors, such as, but not limited to, motion, torque, and speed, based on continuously tracking of the motor. The processor may analyze inner shaft opening rotation, time, and position to dynamically change a reversal position to create a desired performance. The processor may analyze inner shaft opening rotation, time, and position to dynamically change timing of reversal of the opening in the inner drive shaft in real time to create a desired performance. The processor may control timed duty cycles to control inner drive shaft rotation to control alignment of the opening in the inner drive shaft with the opening in the outer housing to alternate between nearly but less than full open and nearly but less than completely closed positions at different timed duty cycles to impact flow rates and clogging. The processor may control inner drive shaft rotation to restrict alignment of the opening in the inner drive shaft with the opening in the outer housing so the windows never fully align thereby mimicking a slit opening. The processor may control inner drive shaft rotation to maximize torque thereby creating more efficient cutting profile without increasing rotational speed.

An advantage of the system is that the system continuously tracks the position of the motor and dynamically adjusts the rotary motion of the inner drive shaft to efficiently cut material, such as, but not limited to, tissue, bone, cartilage and the like.

Another advantage of the system is that the system, when operating in oscillation mode, dynamically adjusts a reversal position to prevent or eliminate an out of phase condition of the opening in the inner drive shaft.

Yet another advantage of the system is that the system, when operating in oscillation mode, dynamically adjusts a reversal position to maximize momentum and torque for the opening in the inner drive shaft.

Another advantage of the system is that the system may create pulsed flow rates that serve to flush the lines and further prevent clogging.

Still another advantage of the system is that the system in oscillation mode is not locked into a single reversal position. Instead, the system may dynamically identify a reversal position from multiple reversal positions before rotating in a reverse direction.

Another advantage of the system is that the system may operate as a closed loop system or as an open loop system.

Yet another advantage of the system is that the processor may be configured to control the motor to control oscillation factors of motion, torque, and speed.

These and other embodiments are described in more detail below.

DETAILED DESCRIPTION

As shown in FIGS. 1-5, a medical device system 10 configured to dynamically control a shaver window opening 42 via controlling rotational position of an opening 12 in an inner drive shaft 14 relative to an opening 16 in an outer housing 18 based on continuously tracking of a motor 20 coupled to the inner drive shaft 14 is disclosed. The medical device system 10 may include a shaver 22 at a distal end 24 and an aspiration system 26 configured to aspirate material through the inner drive shaft 14. A processor 28 of the medical device system 10 may control rotational motion of the inner drive shaft 14 based on continuously sensing a position of the opening 12 in the inner drive shaft 14 to reduce clogs and increase cutting effectiveness of the system 10. By continuously monitoring the medical device system 10, the processor 28 can correct out of phase conditions in oscillation mode to prevent poor cutting conditions and to enable more consistent operation of the device 30 in oscillation mode. The processor 28 can also dynamically determine a reversal position of the opening 12 in the inner drive shaft 14 to create a desired cutting action. In at least one embodiment, the processor 28 can also dynamically determine a reversal position of the opening 12 in the inner drive shaft 14 to create a maximum amount of momentum and torque.

In at least one embodiment, the medical device system 10 may include a handheld rotary medical device 30, as shown in FIGS. 1-4. The device 30 may include a motor 20 in mechanical communication with an inner drive shaft 14 coupled to the motor 20. The inner drive shaft 14 may be coupled directly to the motor 20 or may have one or more other components placing the motor 20 in mechanical communication with the inner drive shaft 14. The motor 20 may be sized to be positioned within the handheld housing 32. The motor 20 may be configured to power a shaver 22 via forward and reverse motor rotation at speeds between a few revolutions per minute (RPMs) and 75,000 RPMs over a wide range of torque profiles, depending on the desired device function and gear ratio.

The processor 28 may control operation of the handheld rotary medical device 30 in accordance with the requirements of a medical procedure being undertaken. For example, if a desired medical procedure requires a smoothing action, as shown in smoothing region 50 of FIG. 5, then the shaver 22 of the device 30 may be operated at a high speed and lower torque with a low fluid flow rate. Similarly, if a desired medical procedure requires course cutting, as shown in coarse cutting region 52 of FIG. 5, then the shaver 22 of the device 30 may be operated at a medium speed, which may be less than the speed in smoothing region 50, and medium torque, which may be greater than the torque in the smoothing region 50, with a medium fluid flow rate, which may be greater than the fluid flow rate in the smoothing region 50. If a desired medical procedure requires planar cutting, as shown in planar cutting region 54 of FIG. 5, then the shaver 22 of the device 30 may be operated at a lower speed, which may be less than the speed in coarse cutting region 52, and higher torque, which may be greater than the torque in the coarse cutting region 52, with a higher fluid flow rate, which may be greater than the fluid flow rate in the coarse cutting region 52.

Throughout different torque versus speed profiles, the processor 28 may monitor and maintain a high degree of positional accuracy with respect to the inner drive shaft 14. Such operation necessitates that the processor 28 track the motor shaft rotations with significant angular precision as well as translation of those angular rotations through a gear system that may or may not have an integer ratio relating the number of motor shaft rotations to one rotation of the inner drive shaft 14. Positional control is primarily required in forward and reverse operation of the inner drive shaft 14 where stopping the motor shaft in a known position is desired to maintain a predetermined percent opening of the window aperture 42.

As shown in FIGS. 1-4, the device 30 may include an elongated outer housing 18 receiving the inner drive shaft 14 such that the inner drive shaft 14 is positioned within the outer housing 18. In at least one embodiment, the device 10 may include a shaver 22 at a distal end 36 of the inner drive shaft 14. The shaver 22 may include at least one opening 12 in an outer wall 38 forming the inner drive shaft 14. The outer housing 18 may include an opening 16 aligned with the shaver 22 at the distal end 36 of the inner drive shaft 14. The opening 12 in the inner drive shaft 14 may have any configuration already invented or yet to be conceived to cut tissue when rotated in one direction or rotated in an opposite direction, or both, such as in an oscillation mode. As such, the opening 12 is not limited to any particular configuration.

Figure 4:
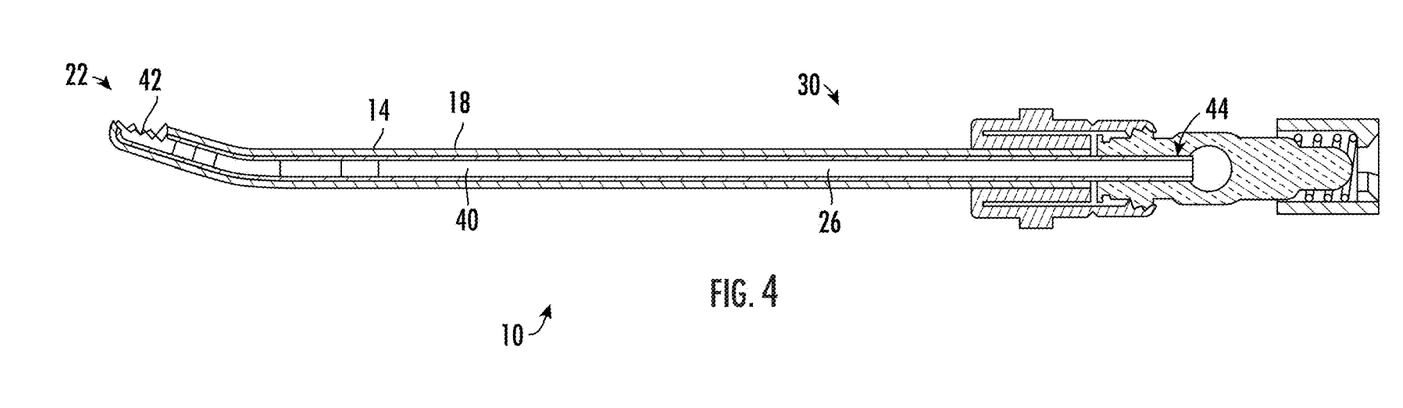
FIG. 4 is cross-sectional side view of the shaver taken as section line 4-4 in FIG. 3.
Figure 5:
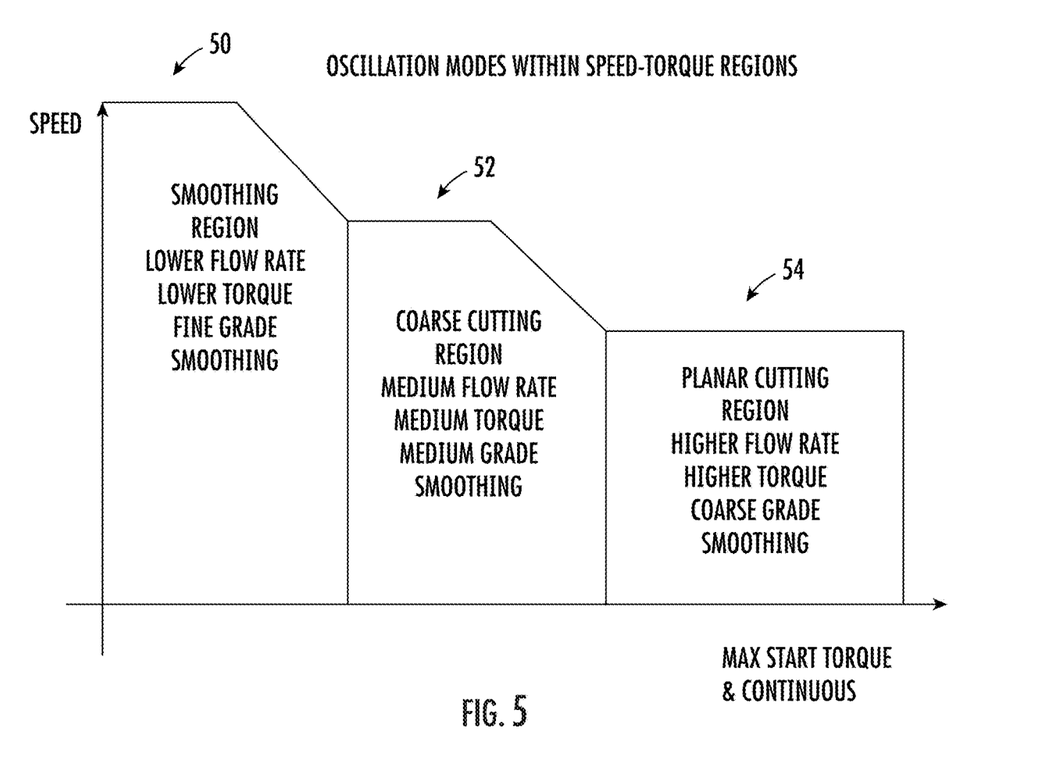
FIG. 5 is a graph of oscillation mode factors and their corresponding operational characteristics of the attached handheld rotary medical device.

The system 10 may include an aspiration system 26, as shown in FIG. 4, with a channel 40 in the inner drive shaft 14. The aspiration system 26 may include a vacuum source capable of creating a vacuum within the channel 40 in the inner drive shaft 14 to aspirate cut tissue, fluids and other materials from a surgical site. The aspiration system 26 may have any appropriate configuration and is not limited to any particular configuration.

Figure 1:
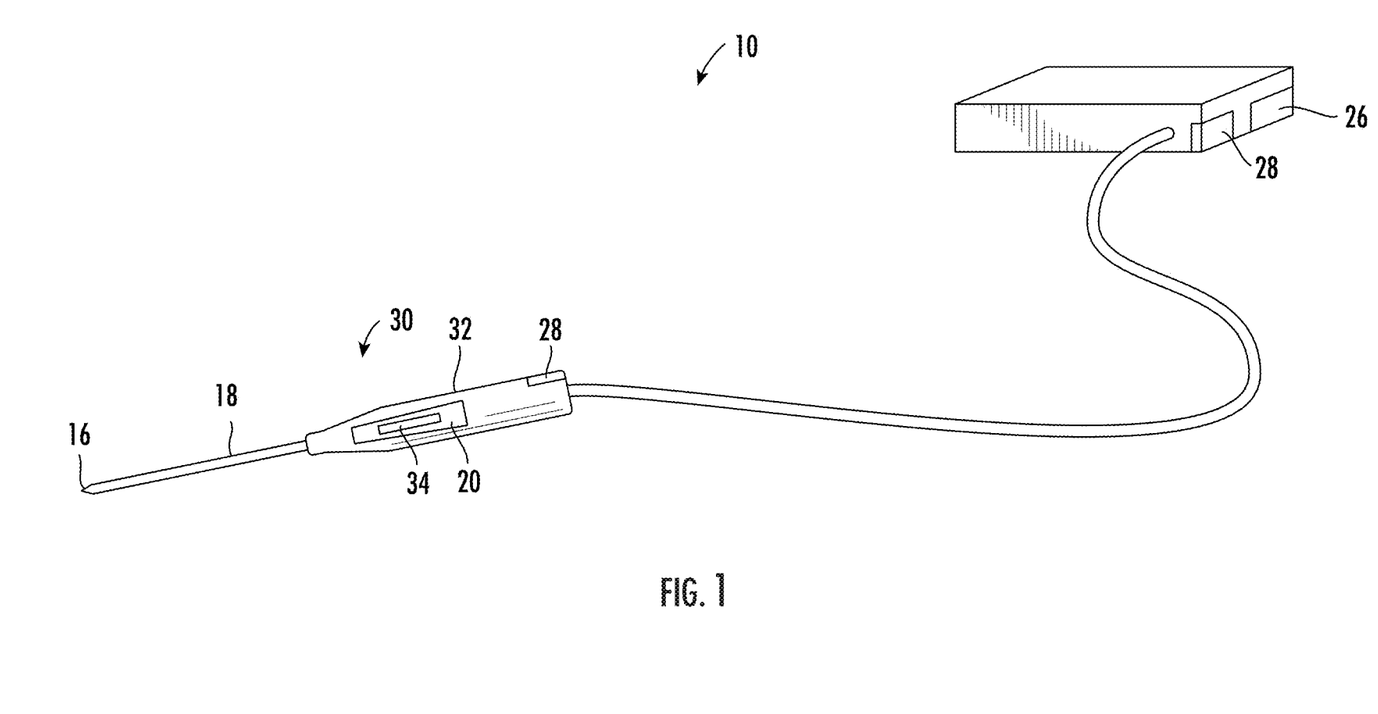
FIG. 1 is a perspective view of a console and a handheld rotary medical device with a shaver.
Figure 2:
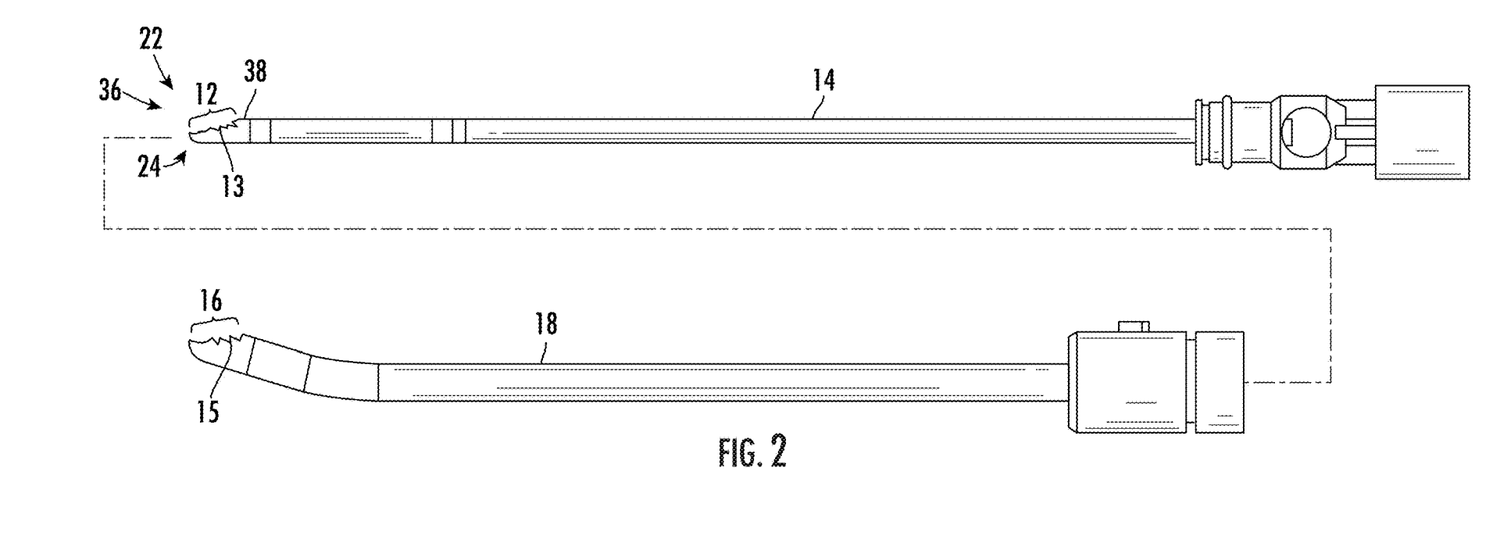
FIG. 2 is an exploded side of the shaver shown in FIG. 1.
Figure 3:
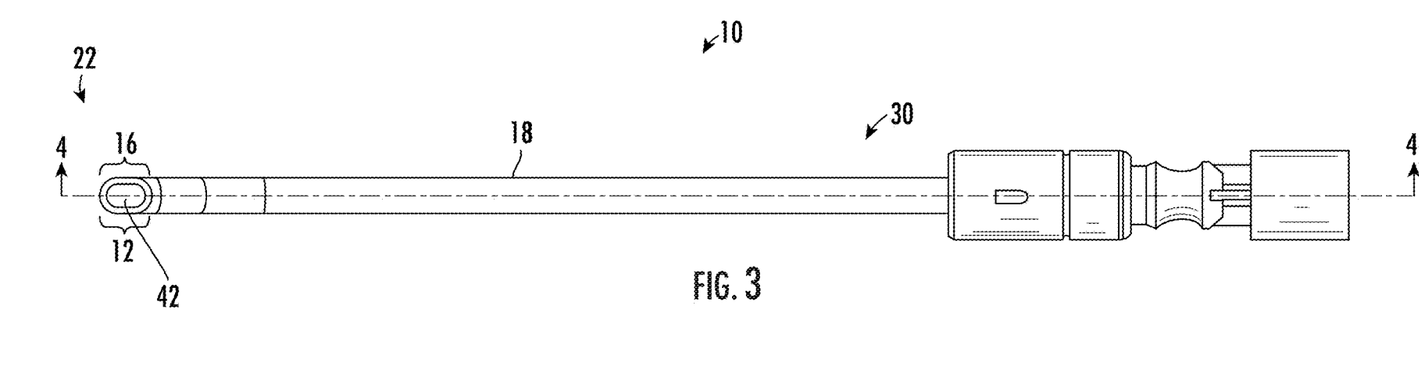
FIG. 3 is an assembled side view of the shaver shown in FIG. 2.

The system 10 may also include a processor 28, as shown in FIG. 1, configured to control driving of the motor 20 and the inner drive shaft 14 in mechanical communication with the motor 20. The processor 28 may be configured to dynamically control the window aperture 42 by controlling positioning of the opening 12 in the inner drive shaft 14 relative to the opening 16 in the outer housing 18 by continuously tracking the motor 20. The processor 28 may be configured to operate the inner drive shaft 14 in an oscillating mode whereby pulsed flow of aspirated material flows through the inner drive shaft 14 to flush the inner drive shaft 14 and prevent clogging. The processor 28 may control oscillation of the shaver 22 via timing in a continuous manner for the purpose of creating pulsed flow rates that flush the lines and further prevent clogging.

The processor 28 may be configured to control the degree of force of the pulsing action ranging from a mild pulsing action to an intense pulsing action by controlling one or more of the numerous variables of control of the oscillation mode, including but not limited to, oscillation speed such as oscillations per second, degree of window opening alignment throughout a single oscillation, the degree of window opening alignment at the reversal position, which can range from 100 percent open to 100 percent closed and any degree of open or closed therebetween, and the like. As such, the pulsing action created by the processor 28 controlling oscillation of the opening 12 in the inner drive shaft 14 relative to the opening 16 in the outer housing 18 creates a pumping action that can be used to prevent line clogging and to clear a line by removing a clog within the line. The more intense the pulsing action, the greater the pumping action created in the line, and vice versa.

The processor 28 may be configured to operate the inner drive shaft 14 in an oscillating mode whereby a reversal position for the inner drive shaft 14 is sequenced to generate a pumping action created by various pulsed flow intensities and flow rates to prevent clogging via reversal positions that may be varied during an oscillation mode. The rotational position of the reversal positions may be varied to create a desired degree of window alignment or misalignment at the reversal position. The greater the window alignment at the reversal position, the greater the flow through the opening 12 such that maximum flow is achieved with 100 percent window alignment, and minimum flow at the reversal position is achieved with 0 percent window alignment when the window 42 is closed. The processor 28 may control the degree of pulsing action by not only controlling the degree of window alignment at the reversal position but may also control the time duration that the inner drive shaft 14 spends at the reversal position. Additionally, the processor 28 may dynamically control the degree of window alignment and the time duration the inner drive shaft 14 spends at the reversal position based upon input received from one or more sensors or other input. As such, the processor 28 may change the time duration that the inner drive shaft 14 spends at the reversal position during shaver device 30 operation. Furthermore, the processor 28 may change all other variables in connection with the window opening 12 during shaver device 12 operation. Moreover, the processor 28 may control the rotational displacement of the window opening 12 on the inner drive shaft 14 relative to the opening 16 in the outer housing 18 to movement in a single rotational direction of less than a complete revolution or greater than or equal to a complete revolution. Similarly, the processor 28 may dynamically change the amount of rotational displacement based on input received from one or more sensors or other input. As such, the processor 28 may control the oscillations between small and large oscillations and therebetween.

The processor 28 may provide continuous position control of the shaver blade movement in one of multiple modes when oscillating the shaver 22. Position control of the shaver blade movement may be accomplished, for example, in one or more ways. In at least one embodiment, one or more sensors 34, such as, but not limited to, hall sensors, may be connected to the motor 20 to track the position of the motor rotor shaft. In another embodiment, hall sensors 34 connected to the motor gearbox shaft that are used to drive an encoder can be read by the processor 28. In yet another embodiment, one or more algorithms may be used to ascertain motor position using one or more sensors 34 to sense back emf and currents in the motor windings. The sensors 34 and processor 28 may be integrated in the handheld device 30 if the handheld device 30 is battery powered. In most embodiments, the system 10 is not battery powered but is powered via connection to a power supply, such as, but not limited to, a municipal power supply and the like. In such configuration, the processor 28 may be positioned in a console that is outside of a housing for the handheld device 30, as shown in FIG. 1. In other embodiments, the processor 28 may even be positioned in a console that is separate from a console associated with the aspiration system 26. Power and hall sensor signals may be transmitted via one or more cables or wirelessly to the processor 28.

In at least one embodiment, the phase position of the motor 20 may be tracked continuously. Monitoring the phase position of the motor 20 continuously enables the processor 28 to dynamically control alignment of the opening 12 of the inner drive shaft 14 with the opening 16 of the outer housing 18, the alignment of which forms a window aperture 42.

Continuously monitoring the phase position of the motor 20 and controlling the alignment of the opening 12 enables the system 10 to overcome a number of conventional problems, including clogging, inefficient usage and the like. For example, the system 10 may reduce clogging of the aspiration system 26 in the inner drive shaft 14 during operation. The system 10 may also control flow rates within the aspiration system 26 and can be operated to be less dependent on the oscillatory speed selections. The system 10 may deliver more consistent blade performance of the opening 12 in the inner drive shaft 14 and less variance related to control methods. The system 10 may also enable the processor 28 to dynamically controlling the window aperture 42 via control of the inner drive shaft 14 to mimic different blade functions, thereby enabling a single drive shaft 14 to create different blade functions instead of different cutting blades being required for different cutting functions.

The processor 28 may control the motor 20 and inner drive shaft 14 such that the processor 28 can create a desired timing of oscillations to the rotation in a continuous fashion for the purpose of creating pulsed flow rates that will serve to flush the aspiration system 26 and prevent clogging. The processor 28 may be configured to operate the inner drive shaft 14 in an oscillating mode that reverses rotational direction of one or more window aperture openings 42. The processor 28 may be configured to operate the inner drive shaft 14 in an oscillating mode that reverses rotational direction at a single or plurality of window aperture openings 42 using a vector which embodies time, rotation and position to define the reversal of direction in a manner that more consistently targets specific user performance parameters. The processor 28 may be configured to operate the inner drive shaft 14 in an oscillating mode in which the inner drive shaft 14 stops at one of multiple possible reversal positions before rotating in a reverse direction.

The processor 28 may operate to create improved cutting efficiency of the shaver 22. The processor 28 may operate the inner drive shaft 14 in an oscillating mode whereby a reversal position for the inner drive shaft 14 is identified to generate maximum momentum of a cutting blade 13 forming the opening 12 in the inner drive shaft 14 for cutting material via the opening 12 in the inner drive shaft 14. In at least one embodiment, the cutting blade forming the opening 12 in the inner drive shaft 14 may be positioned at a reversal position as far rotationally from the opening 16 in the outer housing 18 as possible to generate maximum momentum in the cutting blade 13. Cutting efficiency is improved in the system 10 because the system 10 is configured such that reversal positions of the motor 20 may occur at any one of multiple reversal positions. Additionally, because the motor 20 can reverse and start movement in another direction at multiple reversal positions, the processor 28 may choose a reversal position to create a desired amount of momentum, be it a minimum amount of momentum, maximum momentum or somewhere in between. In at least one embodiment, the oscillation movement can be sequenced in a manner that always reverses and starts movement in a direction that allows an edge of the opening 12 of the inner drive shaft 14 forming a blade to be positioned furthest from the opening 16 of the outer housing 18 forming a cutting window to gain momentum before entering the cutting window space. Such configuration will also have the benefit of avoiding momentary motor stalls, also referred to as drop-outs, when big chunks of debris can get lodged in the inner drive shaft 14 at the opening 12 of the inner drive shaft 14.

In at least one embodiment, continuous tracking of the motor 20 by the processor 28 enables the processor 28 to control the inner drive shaft 14 via an open loop system that controls the inner drive shaft 14 based on desired cutting torque as a function of inner drive shaft 14 opening position. The processor 28 may also operate such that the open loop system controls the inner drive shaft 14 based on desired flush cycles as a function of inner drive shaft opening position. In such configuration of an open loop system, the desired flush cycles could be characterized by testing and the oscillation patterns could be optimized and used based on that data. In another embodiment, the processor 28 may operate such that the open loop system controls the inner drive shaft 14 based on desired cutting debris flow rate as a function of inner drive shaft opening position. In such open loop system, the desired cutting debris flow rate could be determined by testing, and oscillation patterns could be optimized and used based on that data. Operating the system 10 as an open loop system enables the system 10 to implement varying degrees of cutting torque, flush cycles and debris flow rate as a function of blade position.

Continuous control of the inner drive shaft 14 rotation may enable the processor 28 to use a multiphase mode to control the oscillation action of the inner drive shaft 14. The multiphase mode refers to another dimension of how different results are obtained with the shaver 22. For example, the processor 28 may control oscillation cycles of inner drive shaft rotation implemented in multiple phases, whereby a first phase could be X cycles of a predominantly closed window opening 42 resulting from misalignment of the opening 12 in the inner drive shaft 14 and the opening 16 in the outer housing 18 at a reversal stop position followed by a second phase of Y cycles of predominantly open window opening 42 resulting from nearly complete alignment of the opening 12 in the inner drive shaft 14 with the opening 16 in the outer housing 18 at another reversal stop position. A predominantly closed window is where window alignment between the opening 12 in the inner drive shaft 14 with the opening 16 in the outer housing 18 at a reversal stop position forming a window that is less than fifty percent open. A predominantly open window is one in which alignment between the opening 12 in the inner drive shaft 14 with the opening 16 in the outer housing 18 at a reversal stop position forming a window that is greater than fifty percent open. The number of X cycles in the first phase could be the same number or a different number that the number of Y cycles in the second phase. The duty cycle of the first phase, such as X cycles, or the duty cycle of the second phase, such as Y cycles, or both, may be altered to vary the opening and closing of the window alignment between the opening 12 in the inner drive shaft 14 with the opening 16 in the outer housing 18 at different rates, thereby creating different profiles with varying degrees of vary flow rate intensity to attempt to unclog the aspiration system 26 and for other reasons. Additionally, the X cycles of the first phase could also be varied to vary the opening and closing of the window at different rates, creating different profiles with varying degrees of flow rate intensities. If density/flow data suggests that an aspiration line is blocked in a closed loop system, a more intense flush cycle might be implemented to see if the line can be cleared. In an open loop system, optimized flush cycles characterized in testing could be used and potentially adjusted by a user.

In at least one embodiment, continuous tracking of the motor 20 by the processor 28 enables the processor 28 to control the inner drive shaft 14 via a closed loop system that controls the inner drive shaft 14 based on sensor input from the aspiration system 26. The processor 28 may also control the inner drive shaft 14 via a closed loop system that controls the inner drive shaft 14 based on sensor input of fluid flow rate in the aspiration system 26. For instance, in the closed loop system, flow rates could be used to increase or decrease the timing of the window open/closed duty cycle via rotation of the inner drive shaft 14. In another embodiment, the processor 28 may control the inner drive shaft 14 via a closed loop system that controls the inner drive shaft 14 based on sensor input of concentration in the aspiration system. The sensor may identify a metric of fluid in the aspiration system 26 such as, but not limited to, consistency, viscosity or the like, or any combination of metrics, of the material being removed from a surgical site. The system 10 may include one or more sensors 44 positioned in the aspiration system 26 to provide feedback of fluid flow rate or concentration, or both, allowing the processor 28 to use adapt an oscillation control algorithm to changing conditions to better prevent clogging or limit flow rates to some predetermined criteria. In the closed loop system, flow rates along with debris density measurements could be used to increase or decrease the timing of the window open/closed duty cycle.

In at least one embodiment, the system 10 may be configured such that the processor 28 is configured to track revolutions of the opening 12 in the inner drive shaft 14 in each direction. By tracking revolutions of the opening 12 in the inner drive shaft 14, the processor 28 may correct out of phasing conditions enabling more consistent control of an oscillation mode, which in turn stabilizes flow rate of the aspiration system 26 and cutting efficiency of the opening 12 in the inner drive shaft 14. By tracking revolutions of the opening 12 in the inner drive shaft 14, the processor 28 may also control oscillation of the inner drive shaft 14 in a way that can create new functionalities with the same shaver 22. Tracking revolutions of the opening 12 in the inner drive shaft 14 also enables the processor 28 to control the inner drive shaft 14 in a more repeatable manner.

The processor 28 may configured to control the motor 20 to operate at target oscillation factors by continuously tracking the motor 20. In at least one embodiment, the processor 28 may control the motor 20 to operate at target oscillation factors including motion, torque, or speed, or any combination thereof. As such, the shaver 22 can function in a number of different capacities with the processor 28 manipulating the oscillation motion, torque, or speed, or any combination thereof, at which the inner drive shaft 14 is operated. The processor 28 may control the inner drive shaft 14 in a number of different operating conditions via continuous position control with sufficient precision to implement multiple reversal positions.

The processor 28 may be configured to analyze inner shaft opening rotation, time, and position to dynamically change a reversal position to create a desired performance. The processor 28 may analyze inner shaft opening rotation, time, and position to dynamically change a timing of reversal of the opening 12 in the inner drive shaft 14 in real time to create a desired performance. The processor 28 may control timed duty cycles to control inner drive shaft rotation and thereby control aligning of the opening 12 in the inner drive shaft 14 with the opening 16 in the outer housing 18 to alternate between nearly full open and nearly completely closed positions at different timed duty cycles to impact flow rates and clogging. The processor 28 may also control inner drive shaft rotation to restrict alignment of the opening 12 in the inner drive shaft 14 with the opening 16 in the outer housing 18 so the window openings 12, 16 never fully align, mimicking a slit opening. The processor 28 may also control the inner drive shaft 14 to maximize torque on the rotating inner drive shaft 14 to create more efficient cutting profiles without increasing rotational speed. Such operating modes can be triggered and adjusted dynamically while operating based on other inputs into the system 10 or a user of the system 10.

The system 10 may be configured to operate the handheld device 30 in a number of different modes. In at least one embodiment, the system 10 may be configured to operate the handheld device 30 in an oscillation mode or a single direction mode. The system 10 may also be configured to operate in an aggressive, efficient or standard operating mode. The aggressive, standard and efficient modes may be standard modes of oscillation that make trade-offs in terms of starting torque and speed. Some modes are targeting operating most efficiently to smooth a surface and other modes are targeting operation for cutting efficiency, much like rough sandpaper is used to shave down a surface and plows through slowly while fine sandpaper is used to smooth a surface and is often done faster till you get to a buffing process that is fast with little to no cutting action at all. Dynamic window lock works with these modes to not only provide the desired cutting efficiency but also to maximize flow rates and reduce clogging while implementing these modes of operation. The processor 28 may adjust operating parameters, such as, but not limited to, position of the cutting blade 13 at the beginning of each oscillation cycle, number of cutting blade 13 revolutions for each oscillation cycle, and cutting blade 13 position at the end of each oscillation cycle. Cutting blade 13 position may be selectable between 0 and 360 degrees of rotation relative to the fixed blade 15 formed by the opening 16 of the outer housing 18. Establishing an initial fixed opening 16 orientation that defines 0 degrees of rotation may result from rotating a newly installed cutting blade 13 into position using handpiece device 30 input commands, input from a control console or the like. The processor 28 may maintain all positions of the cutting blade 13 relative to the fixed blade 15 orientation until a new fixed blade orientation is established. The system 10 may also include user selections defining acceleration and deceleration profiles for each oscillation cycle, along with a target oscillation speed.

The foregoing is provided for purposes of illustrating, explaining, and describing embodiments of the disclosed devices.

We claim:

1. A medical device system, comprising:
a handheld rotary medical device, comprising:
a motor,
an inner drive shaft coupled to the motor;
an elongated outer housing receiving the inner drive shaft such that the inner drive shaft is positioned within the outer housing;
a shaver at a distal end of the inner drive shaft, wherein the shaver includes at least one opening in an outer wall forming the inner drive shaft; and
wherein the outer housing includes an opening aligned longitudinally with the shaver at the distal end of the inner drive shaft;
an aspiration system with a channel in the inner drive shaft;
a processor configured to control driving of the motor and the inner drive shaft, wherein the processor is configured to dynamically control positioning of a reversal position, during operation of the motor, by dynamically controlling the opening in the inner drive shaft relative to the opening in the outer housing based on continuously tracking the motor to create a desired degree of window alignment or misalignment at any incremental position between and including fully open and fully closed at the reversal position to create desired torque in the inner drive shaft.

2. The medical device system of claim 1, wherein the processor is configured to operate the inner drive shaft in an oscillating mode whereby a pulsed flow of aspirated material flows through the inner drive shaft to flush the inner drive shaft and prevent clogging.

3. The medical device system of claim 1, wherein the processor is configured to operate the inner drive shaft in an oscillating mode that reverses rotational direction of at least one window aperture opening.

4. The medical device system of claim 3, wherein the processor is configured to operate the inner drive shaft in an oscillating mode that reverses rotational direction of at least one window aperture opening using a vector that embodies time, rotation and position to define a reversal of direction in a manner that targets specific user performance parameters.

5. The medical device system of claim 1, wherein the processor is configured to operate the inner drive shaft in an oscillating mode in which the inner drive shaft stops at one of multiple of reversal positions before rotating in a reverse direction.

6. The medical device system of claim 1, wherein the processor is configured to operate the inner drive shaft in an oscillating mode whereby the reversal position for the inner drive shaft is identified to generate maximum momentum for cutting material via the opening in the inner drive shaft.

7. The medical device system of claim 1, wherein continuous tracking of the motor by the processor enables the processor to control the inner drive shaft via an open loop system that controls the inner drive shaft based on desired cutting torque as a function of inner drive shaft opening position.

8. The medical device system of claim 1, wherein continuous tracking of the motor by the processor enables the processor to control the inner drive shaft via an open loop system that controls the inner drive shaft based on desired flush cycles as a function of inner drive shaft opening position.

9. The medical device system of claim 1, wherein continuous tracking of the motor by the processor enables the processor to control the inner drive shaft via an open loop system that controls the inner drive shaft based on desired cutting debris flow rate as a function of inner drive shaft opening position.

10. The medical device system of claim 1, wherein continuous tracking of the motor by the processor enables the processor to control the inner drive shaft via a closed loop system that controls the inner drive shaft based on sensor input from the aspiration system.

11. The medical device system of claim 1, wherein the processor is configured to track revolutions of the opening in the inner drive shaft in each direction to correct out of phasing conditions enabling more consistent control of an oscillation mode, which stabilizes flow rate.

12. The medical device system of claim 1, wherein the processor is configured to control the motor for oscillation factors based on continuously tracking the motor.

13. The medical device system of claim 1, wherein the processor analyzes inner shaft opening rotation, time, and position to dynamically change the reversal position to create a desired performance.

14. The medical device system of claim 1, wherein the processor controls timed duty cycles of inner drive shaft rotation to control alignment of the opening in the inner drive shaft with the opening in the outer housing to alternate between nearly but less than full open and nearly but less than completely closed positions at different timed duty cycles to impact flow rates and prevent clogging.

15. The medical device system of claim 1, wherein the processor controls inner drive shaft rotation to restrict alignment of the opening in the inner drive shaft with the opening in the outer housing so the windows never fully align mimicking a slit opening.

16. The medical device system of claim 1, wherein the processor controls inner drive shaft rotation via a multiphase mode which includes at least two phases with a first phase having a predominantly open window in a first reversal position and a second phase having a predominantly closed window in a second reversal position.

17. The medical device system of claim 16, wherein the processor controls operation in the multiphase mode such that a duty cycle of the first phase is adjusted to vary flush cycle intensities within the aspiration system.

18. The medical device system of claim 16, wherein the processor controls operation in the multiphase mode such that a number of cycles within each first phase may be varied to vary flow rate intensity.

19. The medical device system of claim 1, wherein the processor is configured to operate the inner drive shaft in an oscillating mode that correct an out of phase condition in the oscillating mode.

20. The medical device system of claim 1, wherein the processor is configured to operate the inner drive shaft in an oscillating mode in which the inner drive shaft stops at one of any reversal positions before rotating in a reverse direction such that the system is not limited to a single reversal position.

21. The medical device system of claim 1, wherein continuous tracking of the motor by the processor enables the processor to control the inner drive shaft to create maximum momentum and torque in the inner drive shaft.

22. The medical device system of claim 1, wherein continuous tracking of the motor by the processor enables the processor to control oscillation factors of motion, torque and speed.

23. A medical device system, comprising:
a handheld rotary medical device, comprising:
  a motor,
  an inner drive shaft coupled to the motor;
  an elongated outer housing receiving the inner drive shaft such that the inner drive shaft is positioned within the outer housing;
  a shaver at a distal end of the inner drive shaft, wherein the shaver includes at least one opening in an outer wall forming the inner drive shaft; and
  wherein the outer housing includes an opening aligned longitudinally with the shaver at the distal end of the inner drive shaft;
an aspiration system with a channel in the inner drive shaft;
a processor configured to control driving of the motor and the inner drive shaft, wherein the processor is configured to dynamically control positioning of a reversal position, during operation of the motor, by dynamically controlling the opening in the inner drive shaft relative to the opening in the outer housing based on continuously tracking the motor to create a desired degree of window alignment or misalignment at any incremental position between and including fully open and fully closed at the reversal position to create desired torque in the inner drive shaft;

wherein the processor is configured to operate the inner drive shaft in an oscillating mode whereby a pulsed flow of aspirated material flows through the inner drive shaft to flush the inner drive shaft and prevent clogging; and wherein the processor is configured to control the motor for oscillation factors based on continuously tracking of the motor.

24. A medical device system, comprising:

a handheld rotary medical device, comprising:
- a motor,
- an inner drive shaft coupled to the motor;
- an elongated outer housing receiving the inner drive shaft such that the inner drive shaft is positioned within the outer housing;
- a shaver at a distal end of the inner drive shaft, wherein the shaver includes at least one opening in an outer wall forming the inner drive shaft; and
- wherein the outer housing includes an opening aligned longitudinally with the shaver at the distal end of the inner drive shaft;
- an aspiration system with a channel in the inner drive shaft;
- a processor configured to control driving of the motor and the inner drive shaft, wherein the processor is configured to dynamically control positioning of a reversal position, during operation of the motor, by dynamically controlling the opening in the inner drive shaft relative to the opening in the outer housing based on continuously tracking the motor to create a desired degree of window alignment or misalignment at any incremental position between and including fully open and fully closed at the reversal position to create desired torque in the inner drive shaft;

wherein the processor is configured to operate the inner drive shaft in an oscillating mode whereby a pulsed flow of aspirated material flows through the inner drive shaft to flush the inner drive shaft and prevent clogging; and wherein the processor controls inner drive shaft rotation via a multiphase mode which includes at least two phases with a first phase having a predominantly open window in a first reversal position and a second phase having a predominantly closed window in a second reversal position.

* * * * *